United States Patent
Blair (10) Patent No.: US 7,379,178 B2
(45) Date of Patent: May 27, 2008

(54) FLOW THROUGH CELL FOR OPTICAL SPECTROSCOPY

(75) Inventor: Robert W. Blair, Wantima (AU)

(73) Assignee: Varian Australia Pty Ltd, Mulgrave, Victoria (AU)

( * ) Notice: Subject to any disclaimer, the term of this patent is extended or adjusted under 35 U.S.C. 154(b) by 327 days.

(21) Appl. No.: 10/534,793

(22) PCT Filed: Nov. 11, 2003

(86) PCT No.: PCT/AU03/01492

§ 371 (c)(1),
(2), (4) Date: May 12, 2005

(87) PCT Pub. No.: WO2004/044561

PCT Pub. Date: May 27, 2004

(65) Prior Publication Data

US 2007/0052956 A1  Mar. 8, 2007

(30) Foreign Application Priority Data

Nov. 12, 2002 (AU) .............................. 2002952602

(51) Int. Cl.
*G01N 1/10* (2006.01)
*G01J 5/02* (2006.01)

(52) U.S. Cl. ...................... 356/246; 356/244; 250/343; 422/102

(58) Field of Classification Search ................ 356/244, 356/246; 250/343–344; 422/102, 99, 104, 422/58, 70; 435/293.1, 297.2
See application file for complete search history.

(56) References Cited

U.S. PATENT DOCUMENTS 4,188,534 A * 2/1980 Watanabe et al. ........... 250/345

(Continued)

FOREIGN PATENT DOCUMENTS

JP  2001-0526286  2/2001

(Continued)

*Primary Examiner*—Sang Nguyen
(74) *Attorney, Agent, or Firm*—Bella Fishman; Edward H. Berkowitz (57) ABSTRACT

A flow through cell (100) for use in a spectrophotometer for analysis of dissolved chemical substances in a flowing liquid stream is made up of at least an intermediate body member (114) located between two other body members (112, 116). The body members are of regular shape, for example rectangular parallelepiped and are clamped together, for example by machine screws (134, 136). Thus the cell is relatively easily manufacturable. The clamped together body members define a flow through passage which includes a hole (118) through the intermediate body member (114) and a liquid inlet region at one end of the hole and a liquid outlet region at the other end of the hole, which regions may be provided by galleries (150, 152) in sealing gaskets (130, 132) between the body members. The two other body members each include an optically transparent window (142, 146) at an end of the hole (118) thereby providing an optical pathway (A, A') through part of the flow through passage. The liquid inlet and outlet regions at the ends of hole (118) are such that the liquid flow on entering and leaving the optical pathway (A, A') occurs adjacent the optical windows transversely of the flow along the optical pathway. Thus the liquid flow sweeps across the optical windows (142, 146) and flushes the hole (118) of the optical pathway by successive increments of the liquid with minimal mixing.

12 Claims, 5 Drawing Sheets

U.S. PATENT DOCUMENTS

| | | |
|---|---|---|
| 4,374,620 A | 2/1983 | Berick et al. |
| 4,462,962 A * | 7/1984 | Baba et al. .................... 422/58 |
| 4,575,424 A * | 3/1986 | Allington et al. ......... 210/198.2 |
| 4,818,710 A * | 4/1989 | Sutherland et al. .......... 436/527 |
| 4,822,166 A * | 4/1989 | Rossiter ...................... 356/246 |
| 4,886,356 A * | 12/1989 | Paradis ....................... 356/246 |
| 5,062,706 A * | 11/1991 | Magnussen, Jr. ........... 356/246 |
| 5,073,345 A * | 12/1991 | Scott et al. .................... 422/70 |
| 5,357,113 A * | 10/1994 | Liston et al. ............... 250/344 |
| 5,606,412 A * | 2/1997 | Saito et al. ................. 356/246 |
| 6,122,049 A | 9/2000 | Sugiyama et al. |
| 6,444,175 B1 * | 9/2002 | Singh-Gasson et al. ..... 422/102 |
| 6,493,080 B1 * | 12/2002 | Boese ......................... 356/246 |
| 6,586,235 B1 * | 7/2003 | Banes ...................... 435/293.1 |
| 6,867,857 B2 * | 3/2005 | Hobbs ........................ 356/246 |
| 7,204,139 B2 * | 4/2007 | Takayama ................ 73/204.26 |

FOREIGN PATENT DOCUMENTS

| | | |
|---|---|---|
| JP | 2002-350333 | 12/2002 |
| SU | 1149144 A1 | 4/1985 |

* cited by examiner

FLOW THROUGH CELL FOR OPTICAL SPECTROSCOPY

TECHNICAL FIELD

The present invention relates to a flow through cell for use in a spectrophotometer for analysis of dissolved substances in a flowing liquid stream. The invention is particularly useful with high performance liquid chromatography.

BACKGROUND

The following discussion of the background to the invention is included to explain the context of the invention. This is not to be taken as an admission that any of the material referred to was published, known or part of the common general knowledge in Australia as at the priority date established by the present application.

It is frequently useful to detect and to determine the concentrations of various dissolved chemical substances present in varying concentrations in a flowing liquid stream such as, for example, the effluent of a high-performance liquid chromatograph. If such chemical substances absorb light of characteristic wavelengths they can be detected by spectrophotometry. It is convenient to pass the flowing liquid stream (or a representative portion thereof) through a flow through cell for continuous spectrophotometric measurements. To obtain good resolution of different chemical substances eluted from the column of a chromatograph it is important that the effluent stream should undergo as little mixing as possible in its passage through the flow through cell. This is favoured by keeping the volume of the cell small and by ensuring that all parts of the conduit or passage through the cell are efficiently swept by the flowing liquid. An example of a flow cell having such characteristics is disclosed by Berick and Magnussen, Jr. in U.S. Pat. No. 4,374,620 (Feb. 22, 1983). Another example is disclosed by Magnussen, Jr. in U.S. Pat. No. 5,064,287 (Nov. 12, 1991). In the flow cell of each of these disclosures, means are provided adjacent the entrance end of a flow through passage and surrounding that passage to modify the flow characteristics of a liquid entering the passage. Such means evenly distributes the flow circumferentially as it enters the passage to thereby reduce undesirable mixing of the flow. However both of these flow through cells are difficult to manufacture.

DISCLOSURE OF THE INVENTION

An object of the present invention is to provide a relatively easily manufacturable flow through cell for spectrophotometry According to the invention there is provided a flow through cell for use in a spectrophotometer for analysis of dissolved chemical substances in a flowing liquid stream, comprising a plurality of body members including an intermediate body member located between two other body members, the plurality of body members being clamped together and providing a small volume flow through passage, wherein a part of the flow through passage comprises a hole through the intermediate body member together with a liquid inlet region at one end of the hole and a liquid outlet region at the other end of the hole, wherein the two other body members are each associated with an optically transparent window aligned with a respective end of the hole through the intermediate body member thereby providing an optical pathway through said part of the flow through passage, wherein the liquid inlet and liquid outlet regions are provided by respectively, a portion of the flow through passage through which liquid flows into or out of a said region substantially immediately adjacent the optically transparent window transversely of the direction of the hole.

In one embodiment of the invention each respective said portion of the flow through passage is provided by a gallery in a resilient gasket located between facing surfaces of the intermediate body member and one of said other body members wherein the gallery provides a liquid flow path between the hole and an offset inlet/outlet duct in a body member. The gaskets provide a seal between the body members when they are clamped together.

In another embodiment of the invention each respective said portion of the flow through passage is provided by a gallery formed in a body member wherein the gallery provides a liquid flow path between the hole and an offset inlet/outlet duct in a body member. In this embodiment, resilient gaskets may also be provided to seal between adjacent body members when they are clamped together, however such gaskets may be omitted by providing for at least one of two adjacent body members to be formed from a resilient material which will provide the requisite seal when these body members are clamped together. In an embodiment without gaskets, preferably the intermediate body member is made of a suitably resilient material.

In this specification, the word "gallery" is to be understood as defining a space in either a resilient gasket or a body member, such as may be formed for example by an aperture, hole, recess, cavity, channel, duct, or the like, which provides a liquid flow path when that gasket or body member is assembled with another or other body members to enclose the space.

In either of the above described two embodiments, there may be only three body members, namely the intermediate body member having the hole that provides the principal portion of the optical pathway and another body member on either side thereof within each of which is mounted the optically transparent window which is aligned with the hole when the body members are clamped together. If resilient gaskets are provided which contain the galleries, these are sandwiched between the three body members.

In other embodiments, the flow through cell may be formed by five body members, namely the intermediate body member having the hole, a transparent plate on either side thereof, possibly with resilient gaskets sandwiched therebetween, and a further body member on the "outer" side of each transparent plate. The further body members may contain holes aligned with the hole through the intermediate body member. In embodiments of the flow through cell having this combination of body members, the transparent plates provide the optically transparent windows.

Formation of the flow through cell from a plurality of body members, which may be formed from a corrosion-resistant metal such as for example titanium, or from an appropriate engineering plastic such as for example polyether ether ketone, offers several advantages in that appropriately shaped body members can be readily manufactured by machining or moulding. The body members are not of complex shapes being generally of rectangular parallelepiped shape, and are readily clampable together, for example by machine screws or by through bolts with nuts, or by external clamps. The optically transparent windows can be provided by inserting windows of suitable materials into the body members and appropriately sealing them against the high pressure fluid flow through the flow through passage. An example sealing structure is taught by H. T. Magnussen, Jr. in U.S. Pat. No. 5,062,706 (Nov. 5, 1991), however persons skilled in the art will know of other suitable sealing methods. Alternatively, as described above, plates of transparent material can be sandwiched between resilient gaskets and body members to provide windows. The use of resilient gaskets provides for sealing against leakage of flowing liquid, and is particularly advantageous for readily manufacturing a flow through cell to withstand high pressure liquid flows. Thus the invention provides a flow through cell for spectrophotometry that is relatively easily manufacturable.

The use of appropriately shaped galleries in the gaskets or alternatively in a body member abutting a hole in a gasket to direct flowing liquid through the optical pathway part of the flow through passage has been found to provide efficient sweeping or flushing of the optical pathway by successive increments of liquid with minimal mixing. The cross sectional area of a gallery carrying the liquid into, or out of, or between optical paths can be designed to increase or decrease the velocity of the liquid as appropriate for efficient sweeping or flushing of the optical pathway. Thus the invention allows for sensitive detection of light-absorbing substances in a flowing liquid stream while preserving the resolution of different substances present in consecutive parts of the flowing stream.

Preferably the body members also provide a second optical pathway through another part of the flow through passage. This other part of the flow through passage is preferably shorter in length than the first described optical pathway. This feature makes it possible to extend the range of concentration measurements by using two optical paths of different length. For example, if the concentration of a chemical substance is such that it produces an absorbance that is either too high or too low to be measured accurately in one optical pathway a more appropriate absorbance will be measurable in another.

The body members may also provide an optical pathway separated from the flow through passage for a reference beam to be passed through the cell. This optical pathway for passage of a reference beam can be constructed similarly to the optical pathway through the flow through passage such that its optical characteristics are similar.

Further features and advantages of the invention will become apparent from the following description with reference to the accompanying drawings of preferred embodiments thereof, which are given by way of non-limiting example only, to provide for a better understanding of the invention and to show how it may be carried into effect.

DETAILED DESCRIPTION OF EMBODIMENTS

Figure 1A:
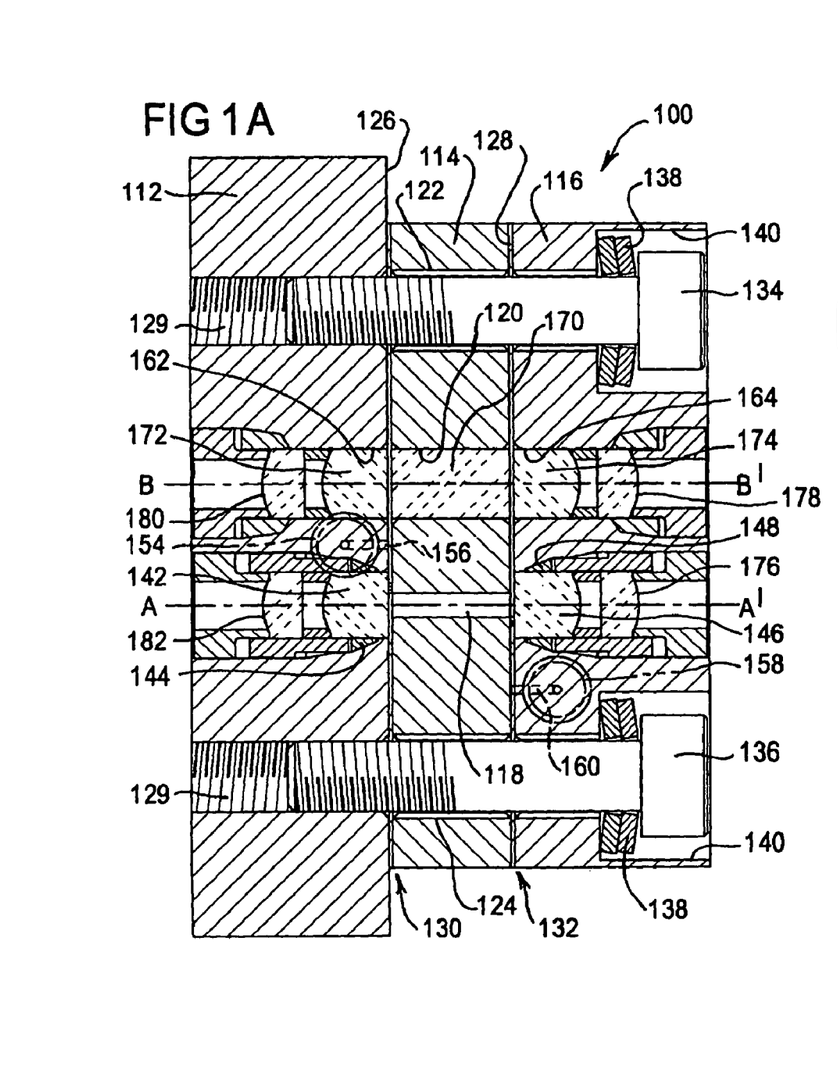
FIG. 1A is a cross-section of an embodiment of the invention that provides a single optical path through the liquid stream and a separate optical path that allows passage of a reference beam.
Figures 1B, 1C:
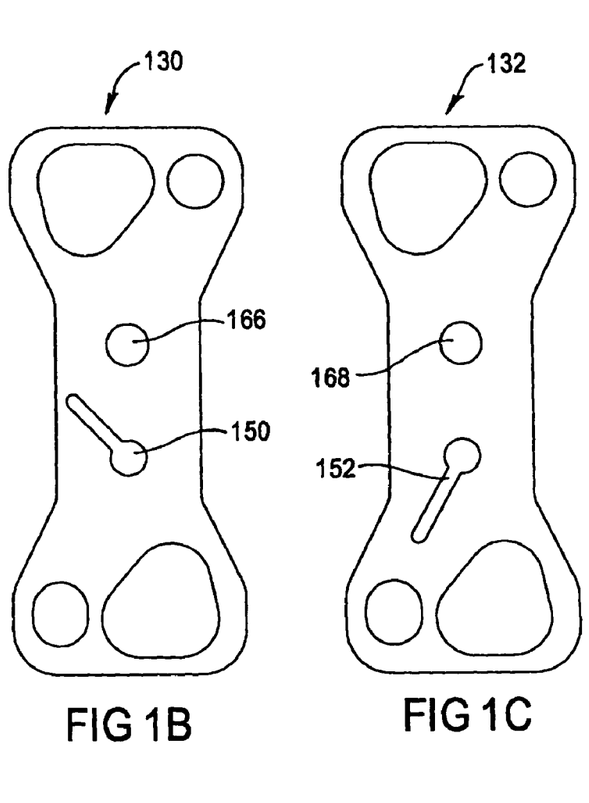
FIGS. 1B and 1C show gaskets of the FIG. 1A embodiment.

Referring first to FIG. 1A, the illustrated flow through cell 100 is constructed from three body members 112, 114, and 116. Body member 114 is an intermediate body member located between body members 112 and 116. It has two parallel flat faces and includes four holes 118, 120, 122 and 124 extending therethrough perpendicularly from one face thereof. Body members 112 and 116 are provided with parallel flat faces 126 and 128 respectively. Body members 112 and 116 include through holes which align with holes 122 and 124 through intermediate body member 114 for assembling the flow through cell as will be described below. The holes through body member 112 may be threaded as indicated by reference 129. To form cell 100 a gasket 130 (see FIG. 1B) made for example from a tetrafluoroethylene hexafluoropropylene copolymer ('FEP', E. I. du Pont de Nemours and Company) is placed against flat face 126 of body member 112, body member 114 is placed against gasket 130, a gasket 132 (see FIG. 1C) is placed against the opposite flat face of body member 114, and flat face 128 of body member 116 is placed against gasket 132. Machine screws 134 and 136 passing through holes 122 and 124 respectively and through the aligned holes in body member 116, corresponding holes in gaskets 130 and 132 and into the threaded holes 129 in body member 112 secure the assembly by clamping the body members together as shown. Washer sets 138 (Belleville washers), within recesses 140 in body member 116, in conjunction with screws 134 and 136 maintain sealing pressure of body members 112, 114 and 116 on gaskets 130 and 132.

Body member 112 is provided with a first optical window assembly 142 including a high pressure circumferential seal 144 (for example as taught in U.S. Pat. No. 5,062,706) and body member 116 is provided with a corresponding second optical window assembly 146 having a high pressure circumferential seal 148. The window assemblies 142 and 146 provide transparent paths through the respective body members 112 and 116. Window assemblies 142 and 146 provide flat transparent surfaces that are level with surfaces 126 and 128 respectively. When cell 100 is assembled as shown in FIG. 1A window 142 aligns with a gallery 150 in gasket 130 and window 146 aligns with a gallery 152 in gasket 132. Galleries 150 and 152 align with the respectively adjacent ends of hole 118, so that an optical path A, A' is provided through cell 100. Body member 112 is provided with a liquid port 154 that is open to a duct 156, which terminates as a hole in flat face 126. Gallery 150 in gasket 130 connects duct 156 to the adjacent end of hole 118 through intermediate body member 114. Similarly, body member 116 is provided with liquid port 158 that is open to a duct 160, which terminates in a hole in flat face 128, and gallery 152 in gasket 132 connects duct 160 to the adjacent end of hole 118. A passage is thereby provided for the flow of liquid between liquid ports 154 and 158 through galleries 150 and 152 and hole 118. Liquid flowing through this passage is in optical pathway A,A' and spectrophotometric measurements can be made on the portion of liquid contained in hole 118 between window assemblies 142 and 146. The path length of light through said portion of liquid is defined by the distance between the corresponding flat faces 126 and 128 of body members 112 and 116 respectively. This distance is principally set by the length of hole 118, that is, by the thickness of intermediate body member 114. The volume of liquid in light path A,A' is principally defined by the length and diameter of hole 118.

Thus FIG. 1A illustrates a flow through cell 100 that comprises a plurality of body members including an intermediate body member 114 located between two other body members 112, 116, the plurality of body members being clamped together (by screws 134, 136) and providing a small volume flow through passage (port 154-duct 156-gallery 150-hole 118-gallery 152-duct 160-port 158), wherein a part of the flow through passage comprises a hole 118 through the intermediate body member 114 together with a liquid inlet region at one end of the hole 118 (gallery 150) and a liquid outlet region (gallery 152) at the other end of the hole 118. The two other body members 112, 116 are each associated with an optically transparent window, respectively 142, 146 aligned with a respective end of the hole 118 through the intermediate body member 114 thereby providing an optical pathway A, A' through said part of the flow through passage. The galleries 150 and 152 which provide the liquid inlet and liquid outlet regions at either end of hole 118 are such that liquid flows into or out of a said region substantially immediately adjacent the optically transparent window 142 or 146 transversely of the direction of the hole 118.

As always in the design of flow cells for optical spectrometry, there is a trade off between providing a very small volume (which favours resolution) and providing sufficient light throughput to obtain an acceptable signal-to-noise ratio. The inventor has found that making hole 118 with a diameter of 1.4 mm and a length of 9.0 mm gives highly satisfactory performance with a specific spectrophotometer used by the inventor. These dimensions make the volume of hole 118 equal to 13.9 microliters. The additional volume of the portions of galleries 150 and 152 at the respective ends of hole 118 brings the total volume of liquid in the optical path A, A' to approximately 15 microliters. Another useful set of dimensions for hole 118 is for example 0.5 mm diameter, 4.0 mm length. Those skilled in the art will appreciate that the dimensions of hole 118 must be selected with due consideration for the beam geometry of the spectrophotometer with which the cell is to be used. Dimensions stated herein are for example only.

A second optical path B,B' is provided through cell 100 parallel to optical path A,A' by way of the hole 120 in intermediate body member 114 and corresponding holes 162 and 164 in body members 112 and 116 respectively, and holes 166 and 168 in gaskets 130 and 132 respectively. An optical spacer 170 is provided in hole 120 in intermediate body member 114, and window assemblies 172 and 174 are provided in body members 112 and 116, so that the optical characteristics of second optical path B,B' are similar to those of optical path A, A'. Second optical path B, B' is useful for the passage of a reference beam through cell 100. Such a reference beam is useful for spectrophotometric measurements of liquid in optical path A,A' as is known in the art. Lenses 176, 178, 180, and 182 form part of the corresponding window assemblies 146, 174, 172 and 142 to focus light through the respective optical paths. In use cell 100 is placed in a spectrophotometer (not shown) in such a way that the sample beam of the spectrophotometer passes along A,A' and the reference beam passes along B,B'. To perform spectrophotometric measurements of a flowing liquid stream one of the two liquid ports 154 and 158 is connected to a source of flowing liquid such as the outlet of the column of a high performance liquid chromatograph. The other of the two liquid ports 154 and 158 is connected to an outlet duct so that the liquid stream can flow away in a controlled manner.

Figure 2A:
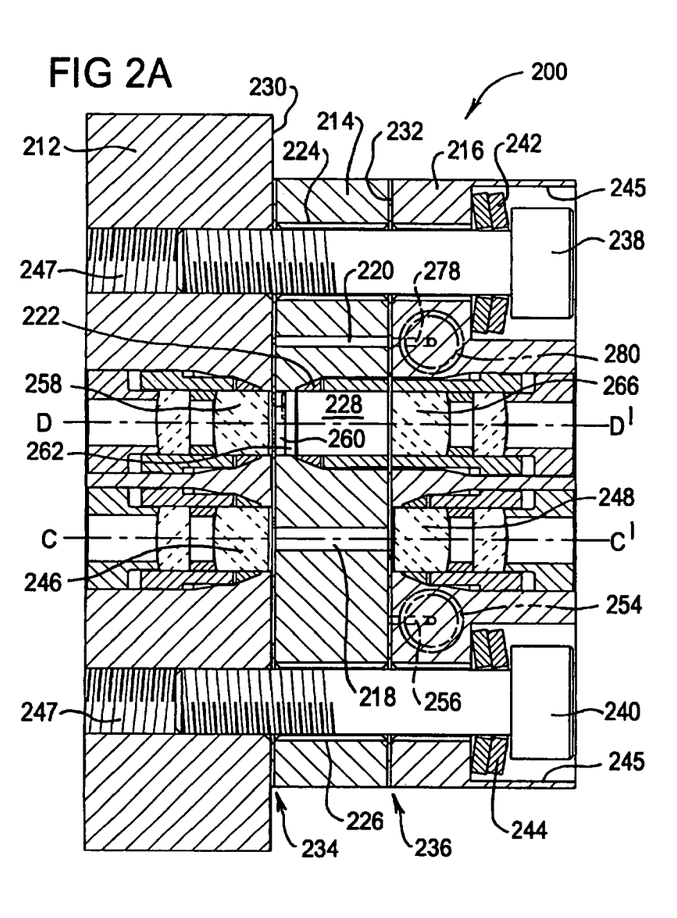
FIG. 2A is a cross-section of an embodiment of the invention that provides two optical paths of different lengths through the liquid stream.
Figure 2B:
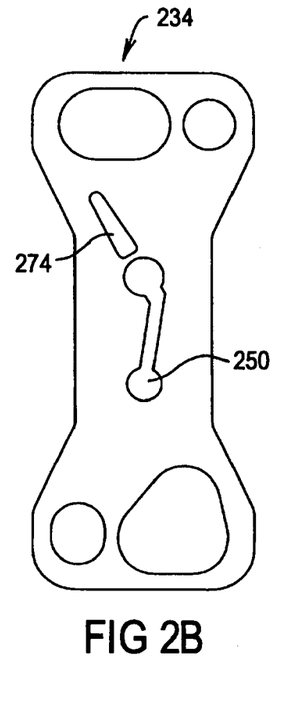
FIGS. 2B and 2C show gaskets of the FIG. 2A embodiment.
Figure 2C:
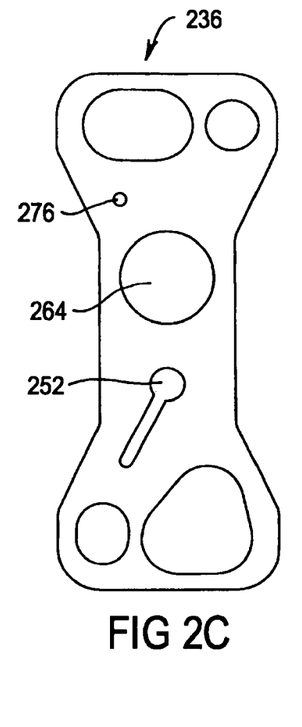
Figure 3A:
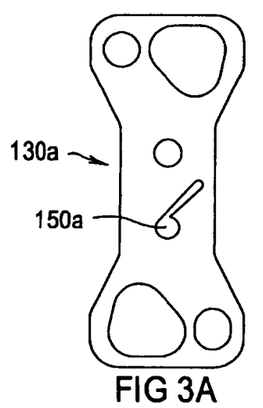
FIGS. 3A to 3D illustrate example gaskets like that of FIG. 1B containing galleries for use in embodiments of the invention.
Figure 3B:
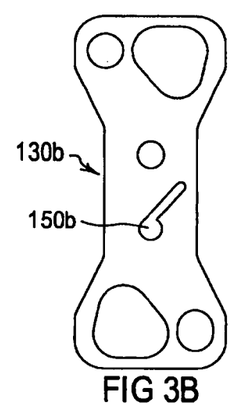
Figure 3C:
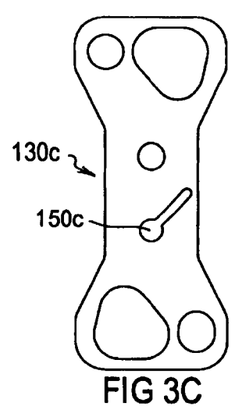
Figure 3D:
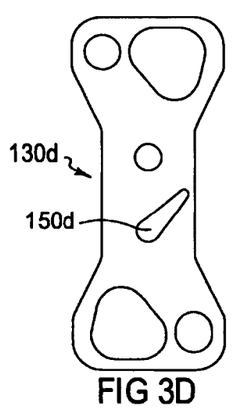
Figure 4A:
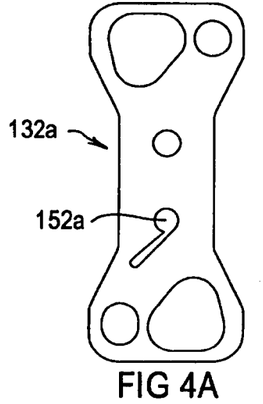
FIGS. 4A to 4D illustrate example gaskets like that of FIG. 1C containing galleries for use in embodiments of the invention.
Figure 4B:
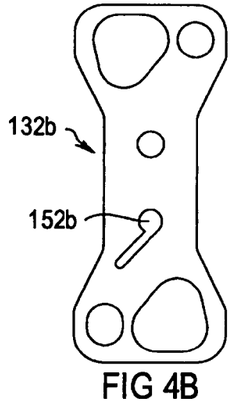
Figure 4C:
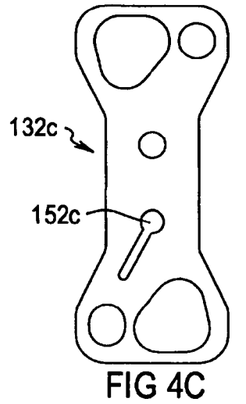
Figure 4D:
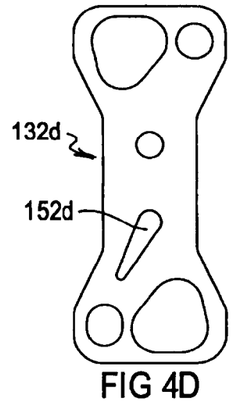

Referring now to FIG. 2A, the illustrated flow through cell 200 is constructed from three body members 212, 214, and 216. Intermediate body member 214 has two parallel flat faces and includes five holes 218, 220, 222, 224, and 226 extending therethrough perpendicularly from one face thereof. Hole 222 is stepped and chamfered as shown to allow for the mounting of an optical spacer/window assembly 228. Window assembly 228 includes a high pressure circumferential seal (for example, as taught in U.S. Pat. No. 5,062,706). Body members 212 and 216 are provided with parallel flat faces 230 and 232 respectively. To form cell 200 a gasket 234 (see FIG. 2B) is placed against flat face 230 of body member 212, body member 214 is placed against gasket 234, a gasket 236 (see FIG. 2C) is placed against the opposite flat face of body member 214, and flat face 232 of body member 216 is placed against gasket 236. Machine screws 238 and 240 passing through holes 224 and 226 respectively in intermediate body member 214 and through corresponding holes in body members 216 and 212 and in gaskets 234 and 236 (similarly to the FIG. 1A embodiment) clamp the assembly together as shown. Similarly to the FIG. 1A embodiment, heads of the screws 238 and 240, along with washers 242, 244 are received within recesses 245 in body member 216 and the screws engage threaded holes 247 in body member 212. The washer sets 242 and 244 (Belleville washers) in conjunction with screws 238 and 240 maintain sealing pressure of body members 212, 214 and 216 on gaskets 234 and 236.

Body member 212 is provided with a first optical window assembly 246 and body member 216 is provided with a corresponding second optical window assembly 248. The window assemblies 246 and 248 provide transparent paths through the respective body members 212 and 216 and provide barriers to the passage of liquid. Window assemblies 246 and 248 provide flat transparent surfaces that are level with surfaces 230 and 232 respectively. When cell 200 is assembled as shown, window 246 aligns with a gallery 250 in gasket 234 and window 248 aligns with a gallery 252 in gasket 236. Galleries 250 and 252 align with the respectively adjacent ends of hole 218, so that a first optical path C, C' is provided through cell 200 as shown.

Figure 5A:
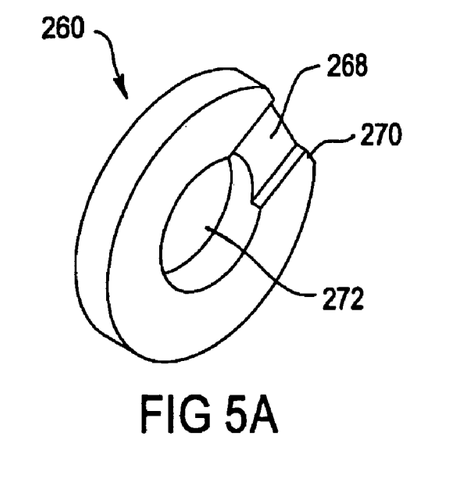
FIGS. 5A and 5B illustrate an annular spacer used in the embodiment of the invention shown in FIG. 2A.
Figure 5B:
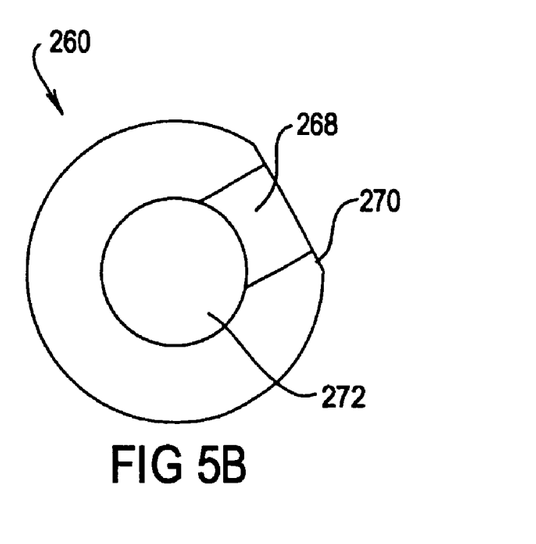

Body member 216 is provided with a liquid port 254 that is open to a duct 256, which terminates as a hole in flat face 232. Gallery 252 in gasket 236 connects duct 256 to the adjacent end of hole 218 through intermediate body member 214. The opposite end of hole 218 is continuous with one end of first gallery 250 in gasket 234. The opposite end of gallery 250 is continuous with the end of hole 222 through intermediate body member 214. Body member 212 is provided with a third window assembly 258 providing an optical path through gallery 250 into hole 222. An annular spacer 260 (see FIGS. 5A and 5B) in hole 222 seals against gasket 234 apart from the gap created by gallery 250. The opposite face of spacer 260 fits against window 262 of optical spacer/window assembly 228 in body member 214. Optical spacer/window assembly 228 provides an optical path through a hole 264 in gasket 236 between body members 214 and 216 to a fourth optical window assembly 266 in body member 216. This provides a second optical path D,D' through cell 200. Portions 268 and 270 (see FIGS. 5A and 5B) of annular spacer 260 adjacent to window 262 of optical spacer/window assembly 228 are cut away to provide a path from the inside 272 of spacer 260 to a second gallery 274 in gasket 234. Second gallery 274 provides a path to the hole 220 through intermediate body member 214, which is continuous with hole 276 in gasket 236. Hole 276 in gasket 236 is continuous with a duct 278 that leads to liquid port 280 in body member 216. A passage is thereby provided for the flow of liquid between liquid port 254 and liquid port 280.

Liquid flows through said passage in optical pathways C,C' and D, D' and separate spectrophotometric measurements can be made on the portion of liquid contained in hole 218 between window assemblies 246 and 248 and on the portion of liquid contained in that portion of the flow path between window assembly 258 and optical spacer/window assembly 228. The path length of light through the portion of liquid in hole 218 is defined by the distance between the corresponding flat faces 230 and 232 of body members 212 and 216 respectively. This distance is principally set by the length of hole 218, that is, by the thickness of body member 214. The volume of liquid in light path C,C' is principally defined by the length and diameter of hole 218. The inventor has found that useful dimensions for hole 218 are for example length 9.0 mm, diameter 1.9 mm, and length 4.0 mm, diameter 2.0 mm when the cell 200 was used with a specific spectrophotometer. Those skilled in the art will appreciate that the dimensions of hole 218 must be selected with due consideration for the beam geometry of the spectrophotometer with which the cell 200 is to be used. Dimensions stated herein are for example only.

The path length of light through the portion of liquid between window assembly 258 and optical spacer/window assembly 228 is principally defined by the distance between the windows of window assembly 258 and window 262 of optical spacer/window assembly 228. This distance is principally set by the thickness of annular spacer 260. The length of window 262 must be such as to provide a firm seal between annular spacer 260 and gasket 234 when annular spacer 260 is pressed against gasket 234 by window 262. The volume of liquid in light path D,D' is principally defined by the length and diameter of the space 272 in annular spacer 260 and that portion of gallery 250 between windows 258 and 262. The inventor has found that a suitable annular spacer 260 has an internal diameter of 2.4 mm and a thickness of 1 mm. This is useful when hole 218 has an internal diameter of 1.9 mm and a length of 9 mm, because the optical path lengths through the flowing liquid C,C' and D,D' are then in the ratio 9:1. Those skilled in the art will appreciate that the dimensions of space 272 in spacer 260 must be selected with due consideration for the beam geometry of the spectrophotometer with which the cell 200 is to be used. Dimensions stated herein are for example only.

In use cell 200 is placed in a special spectrophotometer (not shown) that is provided with two sample beams, as is known in the art (see for example U.S. Pat. No. 5,214,593). Cell 200 is located in such a way that one sample beam of the spectrophotometer passes along C,C' and the other sample beam passes along D,D'. The optical path length through the liquid flow path through C,C' is much greater than that through D,D'. The absorbance is proportional to the optical path length as well as to the concentration of the absorbing species. Consequently it is possible to extend the range of concentration measurements by using two optical paths of different length, as is known. To perform spectrophotometric measurements of a flowing liquid stream, liquid port 254 connected to a source of flowing liquid such as the outlet of the column of a high performance liquid chromatograph, while liquid port 280 connected to an outlet duct so that the liquid stream can flow away in a controlled manner.

FIGS. 3A-3D and 4A-4D show various shapes 150$a$-$d$ and 152$a$-$d$ for galleries 150 and 152 respectively (in gaskets 130 and 132 as in FIGS. 1B and 1C) that have been tested by the inventor. In all of them the wider ends of galleries 150 and 152 open into hole 118 when cell 100 of FIG. 1A is assembled as previously described. The narrower end of each gallery 150 and 152 opens into the associated duct 156 or 160 respectively of cell 100. The shapes shown for galleries 150 and 152 were tested to determine whether or not the different flow characteristics that were expected to result from the different shaped galleries had any effect on the performance of the flow cell 100. No such effect was found. It was concluded that all of the different shapes shown provided adequate flushing of the cell 100 for the flow rates tested.

Figure 9:
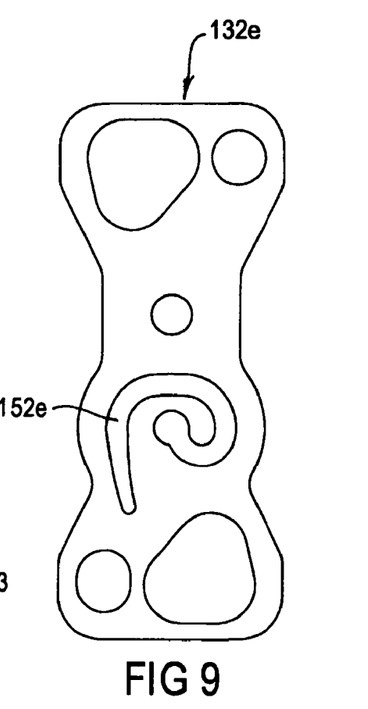
FIG. 9 illustrates another example gasket containing a spiral shaped gallery for use on the inlet side of a flow through passage in embodiments of the invention.

However there is an advantage to be had by making the gallery in the gasket on the inlet side of the flow through passage of a cell 100 generally in the form of a spiral, for example as shown by gallery 152$e$ in the gasket 132$e$ illustrated by FIG. 9 (the FIG. 9 gasket is similar to the FIGS. 4A-4D gaskets). This is so that the incoming liquid spends somewhat more time travelling through the gallery 132$e$ than it otherwise would. The reason for this is that there is a slight difference in temperature between the cell and the liquid coming into the cell from the chromatograph. This temperature difference results in the incoming liquid having a slightly different density, and hence refractive index, from the liquid already in the cell. The rate of delivery of liquid into the cell is not completely uniform, because of mechanical pulsations in the pumps that drive the liquid through the chromatograph. If there is also a temperature difference between the pumped liquid and the cell, this variable rate of delivery results in a variable baseline, which is clearly undesirable. The inventor found that the gallery 132$e$ substantially in the form of a spiral allows the temperature of the incoming liquid to approach that of the cell, resulting in a notably more stable baseline. It is not critical that the gallery 132$e$ be exactly a spiral, merely that it provides a smooth elongated pathway for the liquid.

Figure 6:
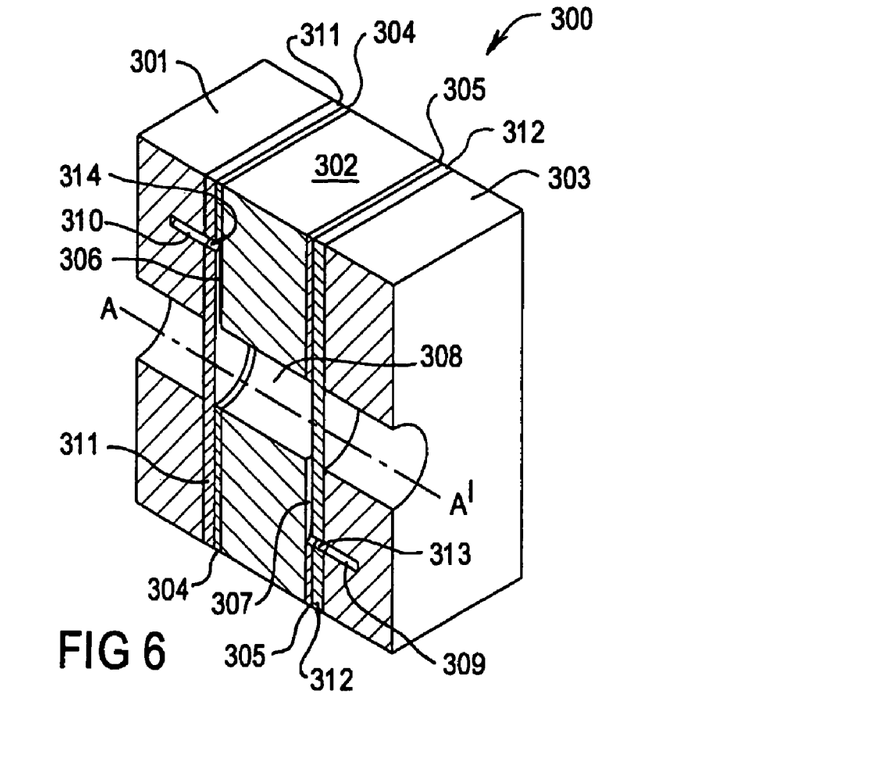
FIG. 6 is a schematic cross sectioned isometric view of part of an embodiment of the invention having flat transparent plates as windows.
Figure 7:
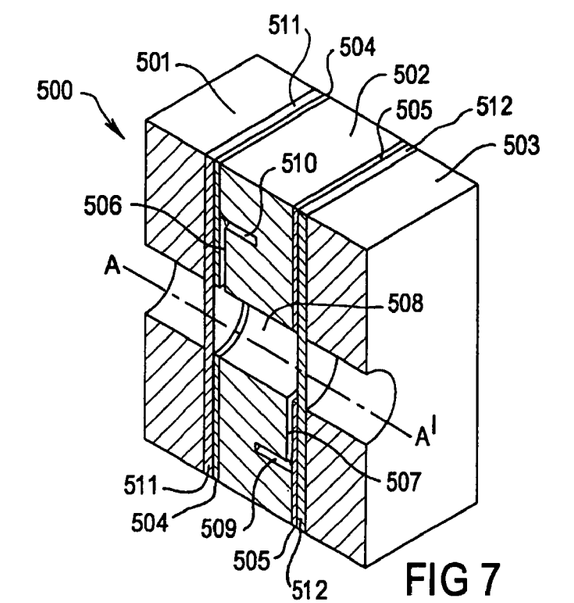
FIG. 7 is a schematic cross sectioned isometric view of part of an embodiment of the invention having flat transparent plates as windows and having galleries formed in a body member rather than in a gasket.
Figure 8:
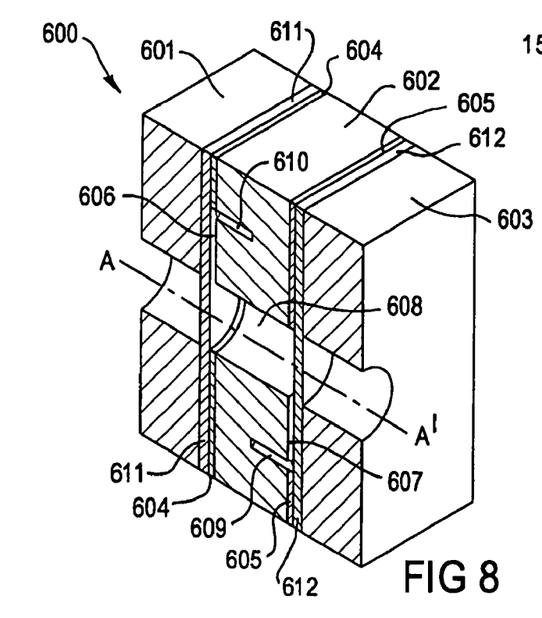
FIG. 8 is a schematic cross sectioned isometric view of part of another embodiment of the invention having flat transparent plates as windows.

FIGS. 6, 7 and 8 are to be understood as showing schematic cross sectioned isometric views of parts of alternative embodiments of the invention including one optical path. It is to be understood that means (not shown) are provided to keep the parts properly clamped together to form a cell as exemplified in the foregoing description, and it is further to be understood that any such cell can contain more than one optical path as also exemplified in the foregoing description.

Referring to FIG. 6, a cell 300 is made up of body members 301, 302 and 303, resilient gaskets 304 and 305 and transparent plates 311 and 312. An optical path A, A' passes through hole 308 in body member 302. Hole 308 forms part of a small volume flow through passage that extends from a liquid port 309 in body member 303 through a hole 313 in transparent plate 312, a gallery 307 in gasket 305, through hole 308, a gallery 306 in gasket 304 and a hole 314 in transparent plate 311 to liquid port 310 in body member 301. A disadvantage of this embodiment of the invention is the need to drill holes 313 and 314 through transparent plates 312 and 311 respectively. This can be avoided by use of alternative embodiments as indicated in FIGS. 7 and 8.

Referring to FIG. 7, cell 500 is made up of body members 501, 502 and 503, transparent plates 511 and 512 and resilient gaskets 504 and 505. An optical path A, A' passes through a hole 508 in intermediate body member 502. Hole 508 forms part of a small volume flow through passage that extends from a liquid port 509 in intermediate body member 502 through a gallery 507 in intermediate body member 502, through the hole 508 and another gallery 506 in the intermediate body member 502 to a liquid port 510 also in intermediate body member 502. In this embodiment of the invention the entry points of galleries 506 and 507 into hole 508 are not immediately adjacent to transparent plates 511 and 512 but are substantially adjacent to the plates 511 and 512 being separated therefrom by the thickness of the resilient gaskets 504 and 505 respectively. This may reduce to some extent the efficiency of flushing the optical cell formed between transparent plates 511 and 512 by liquid flowing between liquid ports 509 and 510. This can be avoided by use of an alternative embodiment as indicated in FIG. 8. Yet another way of avoiding this possible disadvantage is to make the intermediate body member 502 out of a suitably resilient material so that gaskets 504 and 505 can be eliminated Referring to FIG. 8, a flow through cell 600 is made up of body members 601, 602 and 603, transparent plates 611 and 612 and resilient gaskets 604 and 605. An optical path A, A' passes through a hole 608 in the intermediate body member 602. Hole 608 forms part of a small volume flow through passage that extends from a liquid port 609 in the intermediate body member 602 through a gallery 607 in gasket 605, through the hole 608 in intermediate body member 602 and a gallery 606 in the gasket 604 to a liquid port 610 also in intermediate body member 602.

The improvement in resolution obtained by the use of a flow through cell according to the invention is indicated by the results of an experiment in which the effluent of a high performance liquid chromatograph was analysed using a prior art cell (a Varian Prostar 310 15 microliter flow cell) and then the same sample was analysed under the same conditions using a 15 microliter flow cell according to the FIG. 1A embodiment of the invention. The width at half height of the peak obtained with the prior art cell was 9.7 microliters while that with the cell according to FIG. 1A was only 7.0 microliters. The smaller the width at half height, the better the resolution. The figure-of-merit that defines the resolution is called the variance. This was 16.9 microliters squared for the prior art cell and 8.84 microliters squared for the cell according to FIG. 1A.

Furthermore, from all of the above described embodiments it will be appreciated that the flow through cells are relatively easily manufacturable, being made up of a plurality of regular shaped (for example rectangular parallelepiped) body members that are clamped together. Such body members are easily manufactured and their clamping together is readily achievable. Also the liquid flow on entering and leaving the optical pathway between a pair of optically transparent windows occurs substantially immediately adjacent those windows transversely of the flow along the optical pathway. Thus the entering and leaving liquid sweeps across the windows and this action, it is believed, provides adequate flushing or sweeping of the optical pathway by successive increments of the liquid with minimal mixing.

The invention described herein is susceptible to variations, modifications and/or additions other than those specifically described and it is to be understood that the invention includes all such variations, modifications and/or additions which fall within the scope of the following claims.

The invention claimed is:

1. A flow through cell for use in a spectrophotometer for analysis of dissolved chemical substances in a flowing liquid stream, comprising
 a plurality of body members including an intermediate body member located between two other body members, the plurality of body members being clamped together and providing a small volume flow through passage,
 a resilient sealing gasket located between facing surfaces of the intermediate body member and, respectively, each of the two other body members,
 wherein a first portion of the flow through passage comprises a hole through the intermediate body member together with a liquid inlet region at one end of the hole and a liquid outlet region at the other end of the hole,
 wherein each gasket includes a gallery aligned with respective adjacent ends of said hole which provides said first portion of the flow through passage,
 wherein the two other body members are each associated with an optically transparent window aligned with a respective end of the hole through the intermediate body member thereby providing an optical pathway through said first portion of the flow through passage,
 wherein the liquid inlet and liquid outlet regions are provided by respectively, an inlet portion and an outlet portion of the flow through passage through which liquid flows into or out of a said region substantially immediately adjacent the optically transparent window transversely of the direction of the hole.

2. A flow through cell as claimed in claim 1 wherein the gallery in the gasket on an inlet side of the flow through passage is in the form generally of a spiral.

3. A flow through cell as claimed in claim 1 wherein each of said other two body members includes a gallery which provides said inlet and outlet portion of the flow through passage.

4. A flow through cell as claimed in claim 3 wherein at least the intermediate body member, or at least each of the other two body members is resilient to provide for sealing contact between adjacent body members.

5. A flow through cell as claimed in claim 1 wherein the optically transparent window associated with each of the other two body members is a window assembly sealingly mounted within a hole in a body member.

6. A flow through cell as claimed in claim 1 wherein the optically transparent window associated with each of the other two body members is provided by respectively a transparent plate sandwiched between the intermediate body member and one of the other body members.

7. A flow through cell as claimed in claim 1 wherein the body members are of rectangular parallelepiped shape.

8. A flow through cell as claimed in claim 1 wherein the body members are clamped together by screw fasteners.

9. A flow through cell as claimed in claim 8 wherein the screw fasteners pass through holes in one of the other body members and the intermediate body member and engage in threaded holes in the other body member.

10. A flow through cell as claimed in claim 1 wherein the flow through passage includes another portion located between further optically transparent windows associated with the two other body members thereby defining a second optical pathway.

11. A flow through cell as claimed in claim 10 wherein the second optical pathway is shorter than the first defined optical pathway.

12. A flow through cell as claimed in claim 1 wherein the body members also provide an optical pathway separated from the flow through passage for a reference beam to be passed through the cell.

* * * * *